United States Patent [19]

Regel et al.

[11] 4,331,675
[45] May 25, 1982

[54] COMBATING FUNGI WITH TRIAZOLYL-ALKENES

[75] Inventors: Erik Regel; Wilfried Draber; Karl H. Büchel, all of Wuppertal; Paul-Ernst Frohberger, Leverkusen; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 166,268

[22] Filed: Jul. 2, 1980

[30] Foreign Application Priority Data

Jul. 21, 1979 [DE] Fed. Rep. of Germany ....... 2929602

[51] Int. Cl.³ .................... A01N 43/64; C07D 249/08
[52] U.S. Cl. ..................................... 424/269; 424/232; 424/245; 542/431; 542/458
[58] Field of Search ................ 542/458, 431; 548/262; 424/245, 269, 232

[56] References Cited

U.S. PATENT DOCUMENTS

| 4,079,062 | 3/1978 | Van Reet et al. | 424/269 |
|---|---|---|---|
| 4,086,351 | 4/1978 | Balasubramanyan et al. | 424/273 R |
| 4,182,862 | 1/1980 | Chan | 542/458 |
| 4,203,995 | 5/1980 | Funaki et al. | 424/269 |

FOREIGN PATENT DOCUMENTS 3884 9/1979 European Pat. Off. ................ 71/92

Primary Examiner—Alton D. Rollins
Attorney, Agent, or Firm—Sprung, Feife, Horn, Lynch & Kramer

[57] ABSTRACT

A triazolyl-alkene of the formula

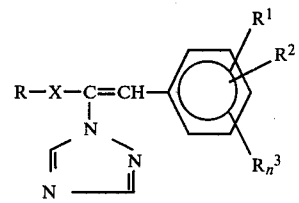

in which
R is an alkyl radical or an optionally substituted phenyl radical,
$R^1$ is a cycloalkyl radical, and
$R^2$ is a hydrogen atom, or
$R^1$ and $R^2$ together, in the o-position relative to each other, are an optionally substituted polymethylene bridge, or, together with the phenyl ring, are naphthyl,
$R^3$ is a halogen atom or an alkyl, alkoxy or halogenoalkyl radical,
n is 0, 1, 2 or 3, and
X is a keto radical or a —CH(OH)-radical,
or an acid addition salt or metal salt complex thereof, which possesses fungicidal activity.

7 Claims, No Drawings

COMBATING FUNGI WITH TRIAZOLYL-ALKENES

The present invention relates to certain new triazolyl-alkene derivatives, to a process for their production and to their use as fungicides.

It has already been disclosed that triazolylalkane derivatives, such as 1-(4-biphenylyloxy)-2-tert.-butyl-carbonyloxy-3,3-dimethyl-1-(1,2,4-triazol-1-yl)butane, have good fungicidal properties. (In this context, see U.S. Pat. No. 4,145,428 issued Mar. 20, 1979.) However, their reaction is not always completely satisfactory, especially when low amounts and concentrations are applied.

The present invention now provides as new compounds, the triazolyl-alkene derivatives of the general formula

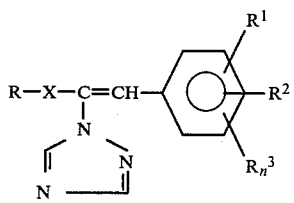

in which
R represents an alkyl group or an optionally substituted phenyl radical,
$R^1$ represents a cycloalkyl group and
$R^2$ represents a hydrogen atom or
$R^1$ and $R^2$ together, in the o-position relative to each other, represent an optionally substituted, multi-membered methylene bridge, or, together with the phenyl ring, represent naphthyl,
$R^3$ represents a halogen atom or an alkyl, alkoxy or halogenoalkyl group,
n is 0, 1, 2 or 3 and
X represents a keto group or a —CH(OH)— group,
and acid addition salts and metal salt complexes thereof.

The compounds of the formula (I) can exist in two geometric isomer forms, depending on the arrangement of the groups which are bonded to the double bond. If X represents the —CH(OH)— grouping, an asymmetric carbon atom is present, so that the compounds of the formula (I) are in this case also obtained in two optical isomer forms. The present invention relates both to the individual isomers and to the isomer mixtures.

The triazolyl-alkene derivatives of the present invention have powerful fungicidal properties. Surprisingly, the substances according to the invention exhibit a better fungicidal activity than the triazolyl-alkone derivatives known from the state of the art, such as 1-(4-biphenylyloxy)-2-tert.-butylcarbonyloxy-3,3-dimethyl-1-(1,2,4-triazol-1-yl)-butane, which are closely related compounds chemically and from the point of view of their action. The substances according to the invention thus represent an enrichment of the art.

Particularly preferred triazolyl-alkene derivatives according to the present invention are those in which R represents a straight-chain or branched alkyl group with 1 to 4 carbon atoms or an optionally substituted phenyl radical, preferred substituents being: halogen, alkyl or alkoxy with in each case 1 to 4 carbon atoms, halogenoalkyl with 1 to 4 carbon atoms and up to 5 halogen atoms, in particular with 1 or 2 carbon atoms and 1 to 3 identical or different halogen atoms (halogen atoms being, in particular, fluorine and chlorine atoms), phenyl, phenoxy, chlorophenyl, chlorophenoxy and nitro, $R^1$ represents a cycloalkyl group with 3 to 7 carbon atoms and $R^2$ represents a hydrogen atom, or $R^1$ and $R^2$ together, in the ortho-position relative to each other, represent an optionally monosubstituted or polysubstituted methylene bridge with 3 to 5 methylene groups, preferred substituents being: halogen (in particular fluorine, chlorine or bromine) and alkyl with 1 to 4 (in particular with 1 or 2) carbon atoms; or, together with the phenyl ring, represent a naphthyl radical, $R^3$ represents a halogen atom (in particular a fluorine, chlorine or bromine atom), a straightchain or branched alkyl or alkoxy group with in each case 1 to 4 carbon atoms or a halogenoalkyl group with 1 to 4 carbon atoms and up to 5 halogen atoms, in particular with 1 or 2 carbon atoms and 1 to 3 identical or different halogen atoms (halogen atoms being, in particular, fluorine and chlorine atoms), n is 0, 1 or 2 and X has the meaning indicated above.

Very particularly preferred compounds of the formula (I) are those in which R represents a tert.-butyl or isopropyl group or a phenyl radical which is optionally monosubstituted or disubstituted by identical or different substituents selected from chlorine, fluorine and methyl; $R^1$ represents a cyclopentyl or cyclohexyl group and $R^2$ represents a hydrogen atom; or $R^1$ and $R^2$ together, in the ortho-position relative to each other, represent a tri-, tetra- or penta-methylene bridge, which is optionally substituted by chlorine or methyl, or, together with the phenyl ring, represent a naphthyl radical; $R^3$ represents a chlorine or fluorine atom or a methyl group; n is 0 or 1 and X has the meaning indicated above.

The following compounds of the general formula (I) may be mentioned specifically, in addition to the compounds mentioned in the preparative examples:

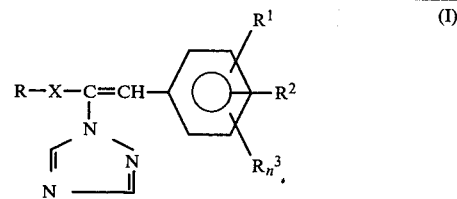

| R | $R^1$ | $R^2$ | $R_n^3$ | X |
|---|---|---|---|---|
| $(CH_3)_3C$ | 4—⟨H⟩ | H | — | CO |
| $(CH_3)_3C$ | 3,4-$(CH_2)_3$ | | — | CO |
| $(CH_3)_3C$ | 3,4-$(CH_2)_4$ | | — | CO |
| $(CH_3)_3C$ | 4—⟨H⟩ | H | — | CO |
| $i-C_3H_7$ | ⟨O⟩ | | — | CO |
| $i-C_3H_7$ | 4—⟨H⟩ | H | — | CO |
| $i-C_3H_7$ | 4—⟨H⟩ | H | — | CO |
| $i-C_3H_7$ | 3,4-$(CH_2)_3$ | | — | CO |
| $i-C_3H_7$ | 3,4-$(CH_2)_4$ | | — | CO |
| Cl—⟨O⟩— | ⟨O⟩ | | — | CO |

-continued

Formula (I):

$$R-X-\underset{\underset{\underset{N}{\parallel}}{N}}{\overset{\phantom{|}}{C}}=CH-\text{Ar}(R^1)(R^2)(R^3_n)$$

where Ar is phenyl bearing R¹, R², R³ₙ; the N-substituent is 1H-1,2,4-triazol-1-yl.

| R | R¹ | R² | R³ₙ | X |
|---|---|---|---|---|
| 4-Cl-C₆H₄- | 4-C₆H₅ | H | — | CO |
| 4-Cl-C₆H₄- | 4-C₆H₁₁ | H | — | CO |
| i-C₃H₇ | 3,4-(CH₂)₃ | | — | CO |
| i-C₃H₇ | 3,4-(CH₂)₄ | | — | CO |
| 3,4-Cl₂-C₆H₃- | C₆H₅ | | — | CO |
| 3,4-Cl₂-C₆H₃- | 4-C₆H₅ | H | — | CO |
| 3,4-Cl₂-C₆H₃- | 4-C₆H₁₁ | H | — | CO |
| 3,4-Cl₂-C₆H₃- | 3,4-(CH₂)₃ | | — | CO |
| 3,4-Cl₂-C₆H₃- | 3,4-(CH₂)₄ | | — | CO |
| 3-CH₃-4-Cl-C₆H₃- | C₆H₅ | | — | CO |
| 3-CH₃-4-Cl-C₆H₃- | 4-C₆H₅ | H | — | CO |
| 3-CH₃-4-Cl-C₆H₃- | 4-C₆H₁₁ | H | — | CO |
| 3-CH₃-4-Cl-C₆H₃- | 3,4-(CH₂)₃ | | — | CO |
| 3-CH₃-4-Cl-C₆H₃- | 3,4-(CH₂)₄ | | — | CO |
| 4-F-C₆H₄- | C₆H₅ | | — | CO |
| 4-F-C₆H₄- | 4-C₆H₅ | H | — | CO |
| 4-F-C₆H₄- | 4-C₆H₁₁ | H | — | CO |
| 4-F-C₆H₄- | 3,4-(CH₂)₃ | | — | CO |
| 4-F-C₆H₄- | 3,4-(CH₂)₄ | | — | CO |
| (CH₃)₃C | 4-C₆H₁₁ | H | — | CH(OH) |
| (CH₃)₃C | 3,4-(CH₂)₃ | | — | CH(OH) |
| (CH₃)₃C | 3,4-(CH₂)₄ | | — | CH(OH) |
| (CH₃)₃C | 4-C₆H₁₁ | H | — | CH(OH) |
| i-C₃H₇ | C₆H₅ | | — | CH(OH) |
| i-C₃H₇ | 4-C₆H₅ | H | — | CH(OH) |
| i-C₃H₇ | 4-C₆H₁₁ | | — | CH(OH) |
| i-C₃H₇ | 4-C₆H₁₁ | H | — | CH(OH) |
| i-C₃H₇ | 3,4-(CH₂)₃ | | — | CH(OH) |
| i-C₃H₇ | 3,4-(CH₂)₄ | | — | CH(OH) |
| 4-Cl-C₆H₄- | C₆H₅ | | — | CH(OH) |
| 4-Cl-C₆H₄- | 4-C₆H₅ | H | — | CH(OH) |
| 4-Cl-C₆H₄- | 4-C₆H₁₁ | H | — | CH(OH) |
| i-C₃H₇ | 3,4-(CH₂)₃ | | — | CH(OH) |
| i-C₃H₇ | 3,4-(CH₂)₄ | | — | CH(OH) |
| 3,4-Cl₂-C₆H₃- | C₆H₅ | | — | CH(OH) |
| 3,4-Cl₂-C₆H₃- | 4-C₆H₅ | H | — | CH(OH) |
| 3,4-Cl₂-C₆H₃- | 4-C₆H₁₁ | H | — | CH(OH) |
| 3,4-Cl₂-C₆H₃- | 3,4-(CH₂)₃ | | — | CH(OH) |
| 3,4-Cl₂-C₆H₃- | 3,4-(CH₂)₄ | | — | CH(OH) |
| 3-CH₃-4-Cl-C₆H₃- | C₆H₅ | | — | CH(OH) |
| 3-CH₃-4-Cl-C₆H₃- | 4-C₆H₅ | H | — | CH(OH) |
| 3-CH₃-4-Cl-C₆H₃- | 4-C₆H₁₁ | H | — | CH(OH) |
| 3-CH₃-4-Cl-C₆H₃- | 3,4-(CH₂)₃ | | — | CH(OH) |
| 3-CH₃-4-Cl-C₆H₃- | 3,4-(CH₂)₄ | | — | CH(OH) |
| 4-F-C₆H₄- | C₆H₅ | | — | CH(OH) |

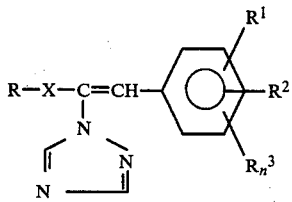

| R | R¹ | R² | R$_n^3$ | X |
|---|---|---|---|---|
| F—⟨O⟩— | 4—⟨H⟩ | H | — | CH(OH) |
| F—⟨O⟩— | 4—⟨H⟩ | H | — | CH(OH) |
| F—⟨O⟩— | | 3,4-(CH$_2$)$_3$ | — | CH(OH) |
| F—⟨O⟩— | | 3,4-(CH$_2$)$_4$ | — | CH(OH) |

According to the present invention there is further provided a process for the production of a compound of the present invention characterized in that a triazoleketone of the general formula

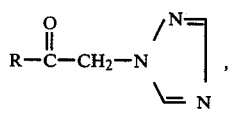

in which R has the meaning indicated above, is reacted with an aldehyde of the general formula

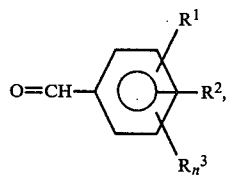

in which R¹, R², R³ and n have the meaning indicated above, in the presence of a solvent and in the presence of a catalyst; and the keto derivative formed, of the formula (I), is, if desired, reduced with a complex hydride, optionally in the presence of a solvent, or with aluminum isopropylate, in the presence of a solvent; and the triazolyl-alkene derivative of formula (I) produced, is converted, if desired, into an acid addition salt thereof or a metal salt complex thereof.

If, for example, pinacolyl-1,2,4-triazole and 2-naphthaldehyde are used as starting substances, the course of the reaction for the preparation of compounds of the invention is illustrated by the following equation:

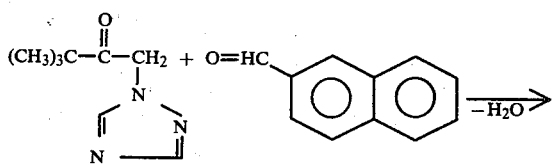

If, 4,4-dimethyl-1-(naphth-2-yl)-2-(1,2,4-triazol-1-yl)-1-penten-3-one and sodium borohydride are used as starting substances, the course of the reaction for the production of compounds of the invention is illustrated by the following equation:

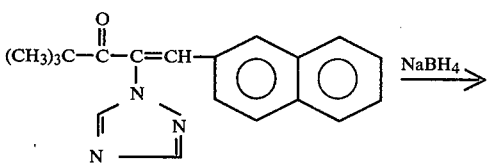

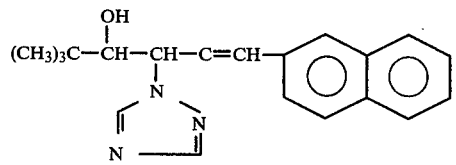

Particularly preferred triazole-ketones to be used as starting compounds of formula (II) for the process according to the invention are those in which R represents those radicals which have already been mentioned for that substituent in connection with the description of the preferred and particularly preferred compounds of the present invention.

The triazole-ketones of the formula (II) are known (see DE-OS (German Published Specification) No. 2,431,407, DE-OS (German Published Specification) No. 2,610,022 and DE-OS (German Published Specification) No. 2,638,470), and they can be obtained by reacting the corresponding halogenoketones with 1,2,4-triazole in the presence of an acid-binding agent.

Particularly preferred aldehydes to be used as starting compounds of formula (III) for the process according to the invention are those in which R¹, R², R³ and n represent those radicals which have already been mentioned for these substituents in connection with the description of preferred and particularly preferred compounds of the present invention.

The aldehydes of the formula (III) are generally known compounds of organic chemistry.

The complex hydrides and aluminum isopropylate which are optionally also required as reaction components are generally known compounds of organic chemistry. Examples of the complex hydrides which may be mentioned are, preferably, sodium borohydride and lithium alanate.

Preferred solvents for the reaction according to the invention are inert organic solvents. These include, preferably, alcohols, such as methanol and ethanol; ethers, such as tetrahydrofuran and dioxane; aliphatic and cycloaliphatic hydrocarbons, such as hexane and cyclohexane; aromatic hydrocarbons, such as benzene, toluene and xylene; halogenated aliphatic and aromatic hydrocarbons, such as methylene chloride and carbon tetrachloride, chloroform, chlorobenzene and dichlorobenzene.

The process according to the invention is carried out in the presence of a catalyst. It is possible to employ any of the acid and, in particular, basic catalysts which can customarily be used, and buffer mixtures thereof. These catalysts include, preferably, Lewis acids, such as boron trifluoride, boron trichloride, tin tetrachloride or titanium tetrachloride; organic bases, such as pyridine and piperidine; and preferably, piperidine acetate.

The reaction temperatures can be varied within a substantial range in carrying out the process according to the invention. In general, the reaction is carried out between 20° and 160° C. preferably at the boiling point of the particular solvent.

In carrying out the process according to the invention, generally 1 to 1.5 moles of aldehyde of the formula (III) and catalytic to 0.2 molar amounts of catalyst are employed per mole of triazole-ketone of the formula (II). Isolation of the compounds of the formula (I) is effected in the customary manner.

If the reduction according to the invention is carried out with complex hydrides, preferred possible diluents are polar organic solvents. These include, preferably, alcohols, such as methanol, ethanol, butanol or isopropanol; and ethers, such as diethyl ether or tetrahydrofuran. The reaction is in general carried out at 0° to 30° C., preferably at room temperature. For this reaction, generally about 1 mole of a complex hydride, such as sodium borohydride or lithium alanate, is employed per mole of the ketone of the formula (I). Isolation of the reduced compounds of the formula (I) is effected in the customary manner.

If aluminum isopropylate is used as the reducing agent, preferred possible diluents for the reaction according to the invention are alcohols, such as isopropanol, or inert hydrocarbons, such as benzene. The reaction temperatures can again be varied within a substantial range; in general, the reaction is carried out between 20° and 120° C., preferably at 50° to 100° C. For carrying out the reaction, generally about 0.3 to 2 moles of aluminum isopropylate are employed per mole of the ketone of the formula (I). To isolate the reduced compounds of the formula (I), the excess solvent is removed in vacuo and the aluminum compounds formed are decomposed with dilute sulphuric acid or sodium hydroxide solution. Further working up is effected in the customary manner.

The following acids can preferably be used for the preparation of physiologically acceptable acid addition salts of the compounds of the formula (I): the hydrogen halide acids (such as hydrobromic acid and in particular hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid), and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are those which, preferably, are derived from the following acids: hydrogen halide acids, such as hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the substances according to the invention can be used with particularly good success for combating cereal diseases, such as powdery mildew of cereal and powdery mildew of barley.

When applied in certain amounts, the substances according to the invention also exhibit a growth-regulating action.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% are generally required at the place of action.

The present invention also provides fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

Preparation of the starting material

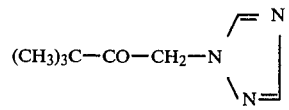

138 g (2 moles) of 1,2,4-triazole were added in portions to 276.4 g (2 moles) of ground potassium carbonate and 296.2 g (2 moles) of α-chloropinacolin in 500 ml of acetone at room temperature, whereupon the internal temperature rose to the boiling point. The reaction mixture was stirred under reflux for 5 hours and then cooled to room temperature. It was filtered and the filtrate was concentrated by distilling off the solvent in vacuo. The oily residue crystallized after adding benzine. 240.8 g (72% of theory) of 3,3-dimethyl-1-(1,2,4-triazol-1-yl)-butan-2-one of melting point 62°–64° C. were obtained.

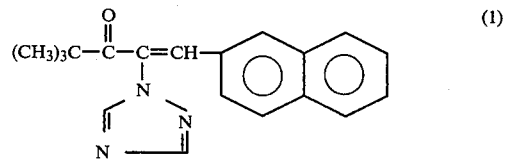

16.7 g (0.1 mole) of pinacolyl-1,2,4-triazole, 15.6 g (0.1 mole) of 2-naphthaldehyde, 1 g of piperidine and 3 g of glacial acetic acid in 50 ml of toluene were heated under reflux, using a water separator, until no further water passed over. After cooling the reaction solution, it was diluted by adding ether and washed with water. The organic phase was dried over sodium sulphate and concentrated by distilling off the solvents in vacuo. The residue was distilled in vacuo. 18 g (59% of theory) of 4,4-dimethyl-1-(naphth-2-yl)-2-(1,2,4-triazol-1-yl)-1-penten-3-one of boiling point 220° C. were obtained.

EXAMPLE 2

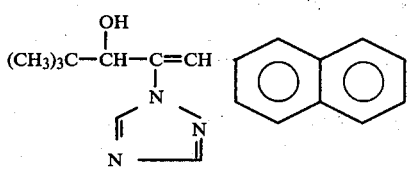 (2)

85 g (0.27 mole) of 4,4-dimethyl-1-(naphth-2-yl)-2-(1,2,4-triazol-1-yl)-1-penten-3-one (Example 1) were taken up in 200 ml of methanol, and 6 g of sodium borohydride were added in portions, while stirring and cooling. When the reaction had ended, the reaction mixture was adjusted to pH 6 and concentrated. The residue was taken up in methylene chloride, washed with saturated sodium bicarbonate solution, dried over sodium sulphate, filtered and concentrated. The oily residue was made to crystallized by adding ether. 41 g (49% of theory) of 4,4-dimethyl-1-(naphth-2-yl)-2-(1,2,4-triazol-1-yl)-1-penten-3-ol of melting point 122°–124° C. were obtained.

The fungicidal activity of the compounds of this invention is illustrated by the following example wherein compound (2) is from Example 2 hereinabove:

The known comparison compound is identified as follows:

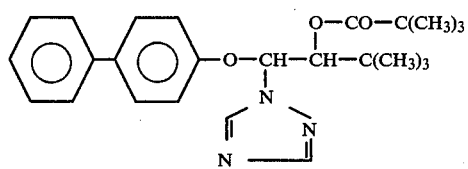

EXAMPLE 3

Shoot treatment test/powdery mildew of cereal/protective (leaf-destructive mycosis).

To produce a suitable preparation of active compound 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei.*

After 6 days' dwell time of the plants at a temperature of 21° to 22° C. and 80 to 90% atmospheric humidity, the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compound exhibited a very good action which was superior to that of the compound (A) known from the prior art: compound (2).

It will be appreciated that the instant specification and examples are set forth by way of illustration and not limitation, and that various modifications and changes may be made without departing from the spirit and scope of the present invention.

What is claimed is:

1. A triazolyl-alkene of the formula

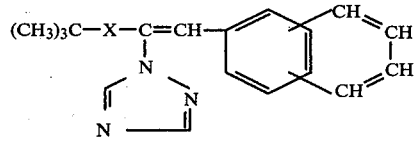

in which X is a keto radical or a —CH(OH)— radical, or a physiologically acceptable acid addition salt thereof with a hydrogen halide acid, phosphoric acid, nitric acid, sulphuric acid, a monofunctional or bifunctional carboxylic acid or hydroxycarboxylic acid or a sulphonic acid, or a metal salt complex thereof in which the metal is copper, zinc, manganese, magnesium, tin, iron or nickel and the anion is derived from hydrochloric, hydrobromic, phosphoric, nitric or sulphuric acid.

2. A compound according to claim 1, in which said compound is 4,4-dimethyl-1-(naphth-2-yl)-2-(1,2,4-triazol-1-yl)-1-penten-3-one of the formula

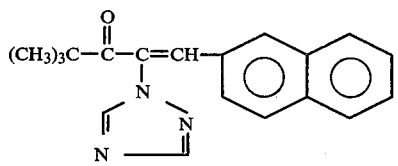

or an acid addition salt or metal salt complex thereof as recited.

3. A compound according to claim 1, in which said compound is 4,4-dimethyl-1-(naphth-2-yl)-2-(1,2,4-triazol-1-yl)-1-penten-3-ol of the formula

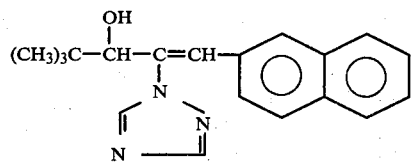

or an acid addition salt or metal salt complex thereof as recited.

4. A fungicidal composition, comprising a fungicidally effective amount of a compound or acid addition salt or metal salt complex thereof according to claim 1 in admixture with a diluent.

5. A method of combating fungi comprising applying to the fungi, or to a habitat thereof, a fungicidally effective amount of a compound or acid addition salt or metal salt complex thereof according to claim 1.

6. The method according to claim 5, in which said compound is 4,4-dimethyl-1-(naphth-2-yl)-2-(1,2,4-triazol-1-yl)-1-penten-3-one of the formula

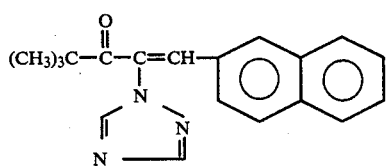
or an acid addition salt or metal salt complex thereof.
7. The method according to claim 5, in which said compound is 4,4-dimethyl-1-(naphth-2-yl)-2-(1,2,4-triazol-1-yl)-1-penten-3-ol of the formula
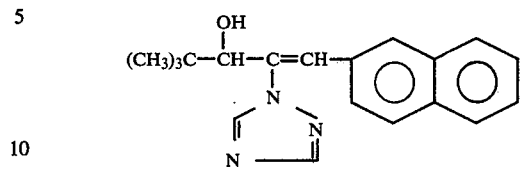
or an acid addition salt or metal salt complex thereof.
* * * * *